(12) United States Patent
Meade et al.

(10) Patent No.: US 11,357,484 B2
(45) Date of Patent: Jun. 14, 2022

(54) MEDICAL DEVICE RETRIEVAL WITH MULTIPLE SNARES

(71) Applicant: Medtronic, Inc., Minneapolis, MN (US)

(72) Inventors: Colin W. Meade, Westmeath (IE); Paula McDonnell, Galway (IE); Francis D. McEvoy, Laois (IE); Rónán Wood, Galway (IE); Kealan E. O'Carroll, Galway (IE); Kenneth C. Gardeski, Plymouth, MN (US); Ronald A. Drake, St. Louis Park, MN (US); Kevin R. Seifert, Forest Lake, MN (US); Brian P. Colin, Shakopee, MN (US); Pierce Vatterott, Eagan, MN (US)

(73) Assignee: Medtronic, Inc., Minneapolis, MN (US)

( * ) Notice: Subject to any disclaimer, the term of this patent is extended or adjusted under 35 U.S.C. 154(b) by 527 days.

(21) Appl. No.: 15/940,600

(22) Filed: Mar. 29, 2018

(65) Prior Publication Data

US 2018/0280058 A1 Oct. 4, 2018

Related U.S. Application Data

(60) Provisional application No. 62/479,019, filed on Mar. 30, 2017.

(51) Int. Cl.
*A61B 17/00* (2006.01)
*A61B 17/34* (2006.01)
*A61B 17/221* (2006.01)

(52) U.S. Cl.
CPC ...... *A61B 17/00234* (2013.01); *A61B 17/221* (2013.01); *A61B 17/3468* (2013.01);
(Continued)

(58) Field of Classification Search
CPC .............. A61B 17/3468; A61B 17/221; A61B 17/32056; A61B 17/22031;
(Continued)

(56) References Cited

U.S. PATENT DOCUMENTS 5,098,440 A * 3/1992 Hillstead .............. A61B 17/221
606/108
5,190,554 A * 3/1993 Coddington, III ...........................
A61B 17/00234
606/1

(Continued)

FOREIGN PATENT DOCUMENTS

WO 2018005549 A1 1/2018

OTHER PUBLICATIONS (PCT/US2018/025326) PCT Notification of Transmittal of the International Search Report and the Written Opinion of the International Searching Authority, dated Jun. 29, 2018, 12 pages.

*Primary Examiner* — Dianne Dornbusch
(74) *Attorney, Agent, or Firm* — Shumaker & Sieffert, P.A.

(57) ABSTRACT

An improved assembly for securing an implantable medical device for retrieval from an implant site includes a plurality of snares, wherein distal openings of a first snare carrier lumen and a second snare carrier lumen have a pre-set offset established therebetween. First and second snare shafts, to which first and second snare loops are coupled, respectively, extend within the corresponding snare carrier lumens such that each loop is located in proximity to the corresponding distal opening of the lumen. The pre-set offset allows an operator to simultaneously position the snare loops around the device; and, when the operator retracts the snare shafts to collapse the snare loops until the loops fit snuggly around the device, the pre-set offset can help to align the device for retrieval.

20 Claims, 13 Drawing Sheets

(52) U.S. Cl.
CPC ............... *A61B 2017/00292* (2013.01); *A61B 2017/00358* (2013.01); *A61B 2017/2212* (2013.01)

(58) Field of Classification Search
CPC .. A61B 2017/00358; A61B 2017/2212; A61B 2017/2215; A61B 2017/2217; A61B 2017/22034; A61B 2017/22035; A61B 2018/1407; A61B 2018/141; A61F 2/95; A61F 2/011; A61F 2002/9511; A61F 2002/9528; A61F 2002/9534
See application file for complete search history.

(56) References Cited

U.S. PATENT DOCUMENTS

| | | | |
|---|---|---|---|
| 5,713,948 A * | 2/1998 | Uflacker | A61F 2/07 606/194 |
| 5,814,052 A * | 9/1998 | Nakao | A61B 17/12013 606/110 |
| 5,928,163 A * | 7/1999 | Roberts | A61B 18/1445 600/567 |
| 7,130,700 B2 | 10/2006 | Gardeski et al. | |
| 7,789,881 B2 * | 9/2010 | Weitzner | A61B 18/14 606/47 |
| 8,509,916 B2 | 8/2013 | Byrd et al. | |
| 8,628,540 B2 | 1/2014 | Freudenthal | |
| 8,992,545 B2 * | 3/2015 | Cahill | A61B 17/0057 606/108 |
| 9,034,006 B2 | 5/2015 | Quinn et al. | |
| 9,126,032 B2 | 9/2015 | Khairkhahan et al. | |
| 9,463,039 B2 * | 10/2016 | Kuroda | A61B 17/221 |
| 9,782,197 B2 * | 10/2017 | Kato | A61B 17/22031 |
| 9,801,651 B2 * | 10/2017 | Harrah | A61B 17/32056 |
| 10,105,533 B2 * | 10/2018 | Grace | A61B 17/32056 |
| 2003/0163129 A1 * | 8/2003 | Lee | A61B 8/0825 606/47 |
| 2004/0059345 A1 * | 3/2004 | Nakao | A61B 17/221 606/113 |
| 2006/0253128 A1 * | 11/2006 | Sekine | A61B 17/122 606/139 |
| 2011/0106107 A1 * | 5/2011 | Binmoeller | A61B 17/32056 606/139 |
| 2011/0282427 A1 * | 11/2011 | Bourang | A61F 2/958 623/1.12 |
| 2012/0172690 A1 | 7/2012 | Anderson et al. | |
| 2013/0006262 A1 * | 1/2013 | Lampropoulos | A61B 17/221 606/113 |
| 2013/0079758 A1 | 3/2013 | Goode et al. | |
| 2014/0188124 A1 | 7/2014 | Lampropoulos et al. | |
| 2015/0051682 A1 | 2/2015 | Schmidt et al. | |
| 2015/0094668 A1 | 4/2015 | Wood et al. | |
| 2015/0283376 A1 * | 10/2015 | Ollivier | A61N 1/0573 606/129 |
| 2015/0306381 A1 | 10/2015 | Schmidt et al. | |
| 2015/0327878 A1 * | 11/2015 | Chu | A61B 17/221 606/127 |
| 2016/0220829 A1 | 8/2016 | Wood | |
| 2017/0028190 A1 | 2/2017 | O'Carroll et al. | |
| 2017/0043158 A1 | 2/2017 | Kelly et al. | |
| 2017/0095662 A1 | 4/2017 | McDonnell et al. | |
| 2017/0136231 A1 | 5/2017 | Kelly et al. | |

* cited by examiner

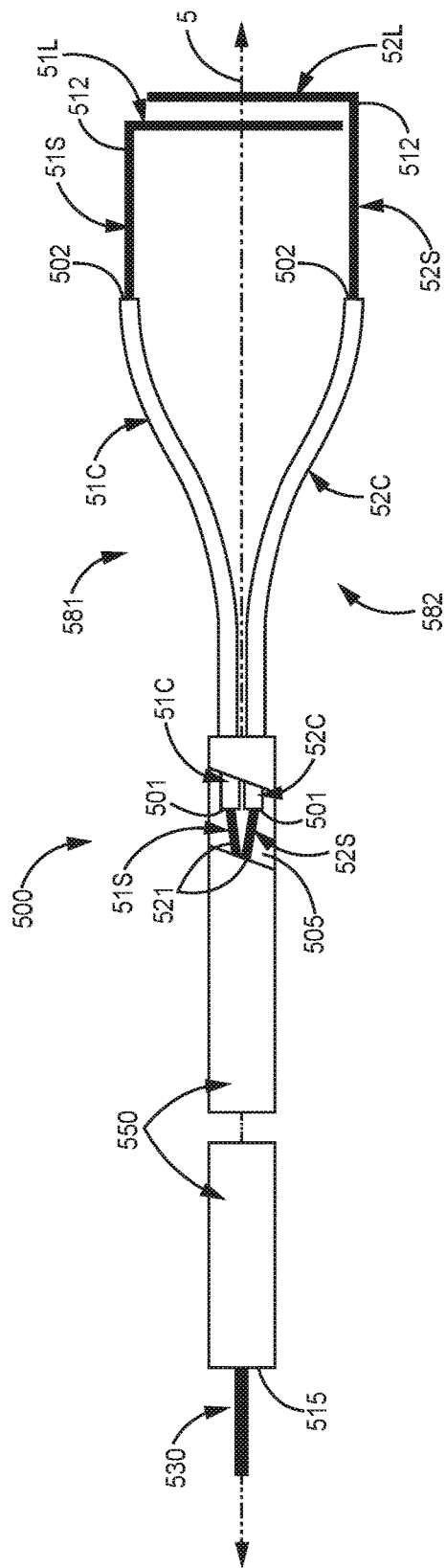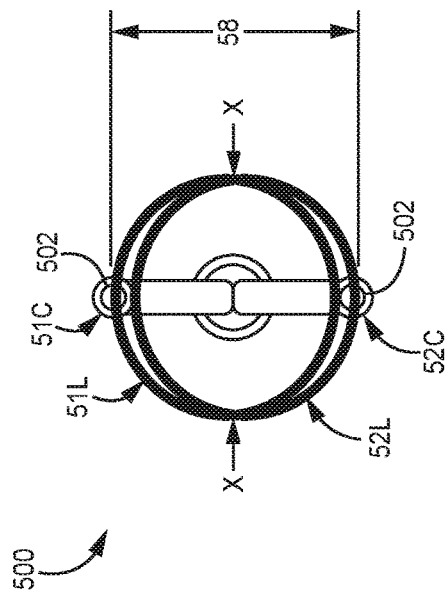
FIG. 5A
FIG. 5B

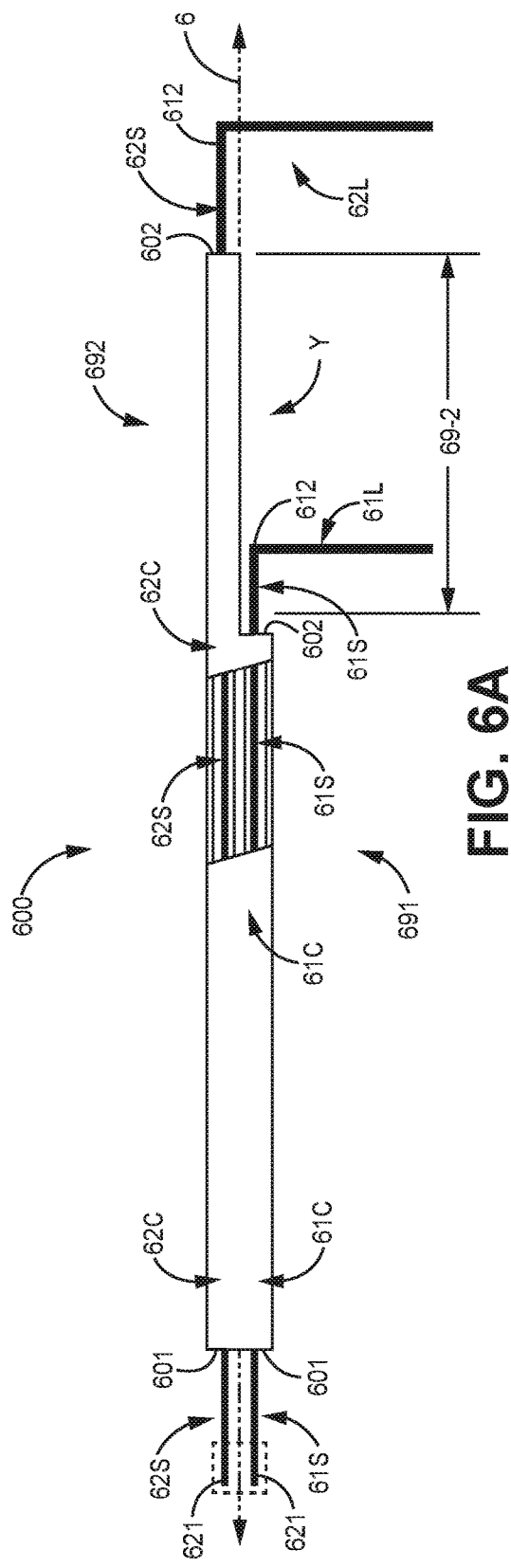
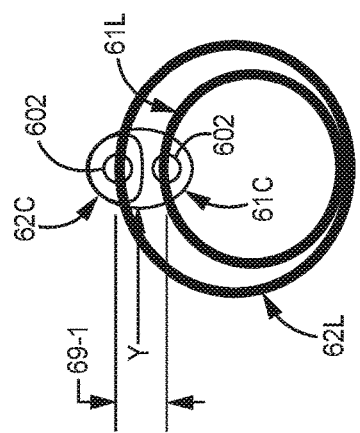

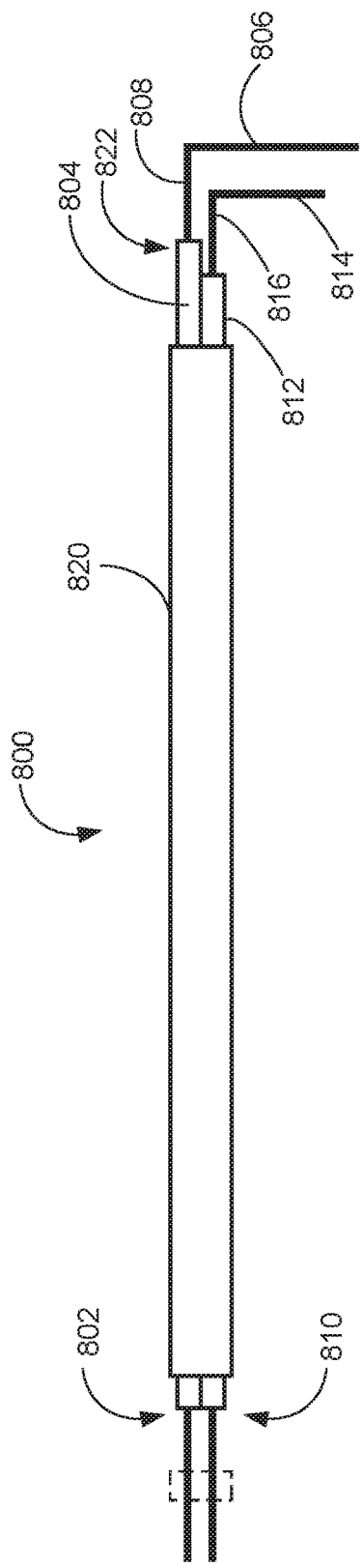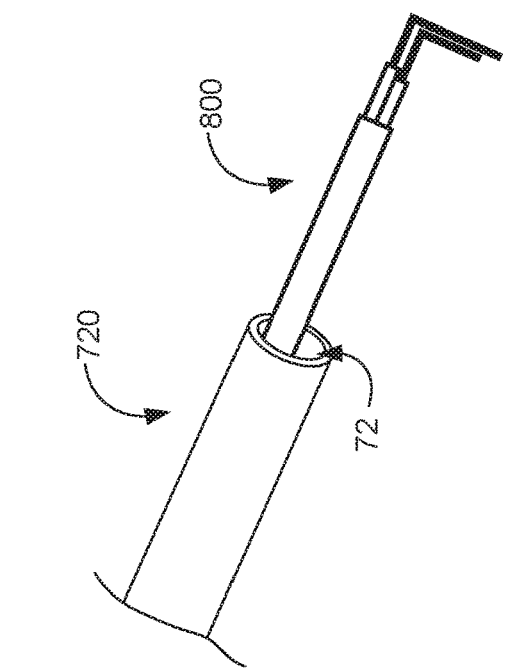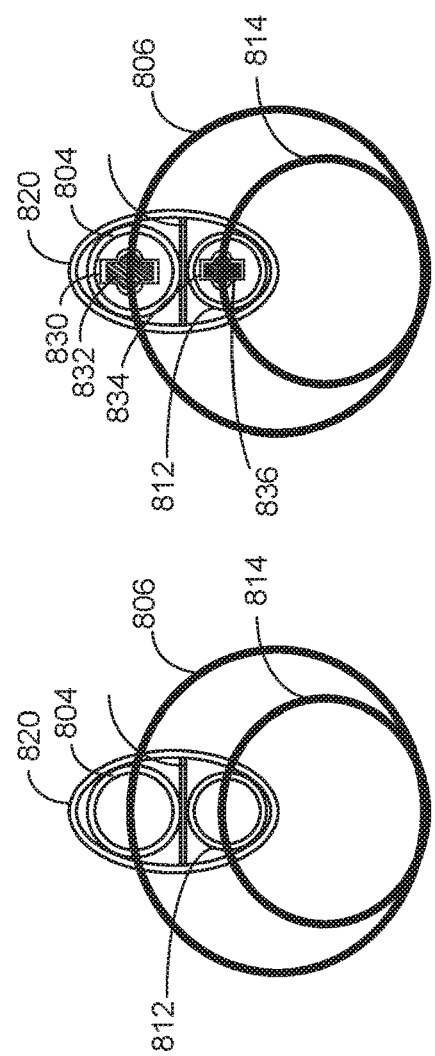

MEDICAL DEVICE RETRIEVAL WITH MULTIPLE SNARES

CROSS-REFERENCE TO RELATED APPLICATIONS

This application claims the benefit of U.S. Provisional Application Ser. No. 62/479,019, filed Mar. 30, 2017, the entire content of which is incorporated by reference herein.

TECHNICAL FIELD

The present disclosure pertains to interventional medical systems, and more particularly to assemblies and methods for securing medical devices for retrieval from implant sites.

BACKGROUND

Some implantable cardiac pacemakers include a pulse generator device to which one or more flexible elongate lead wires are coupled. Such a device is typically implanted in a subcutaneous pocket, remote from the heart, and each of the one or more lead wires extends therefrom to a corresponding electrode, coupled thereto and positioned at a pacing site, either endocardial or epicardial. Mechanical and/or MRI compatibility issues, sometimes associated with elongate lead wires have motivated the development of implantable cardiac pacing devices that are wholly contained within a relatively compact package, the entirety of which is configured for implant in close proximity to the pacing site. Without elongate lead wires, it may be difficult to remove a fully implantable pacing device (if needed) once implanted.

SUMMARY

This disclosure generally relates to retrieving an implantable medical device from an implant site. According to aspects of this disclosure, an assembly includes a plurality of snares, wherein each snare of the plurality of snares includes an elongate carrier, a loop, and an elongate shaft, a distal end of which is coupled to the loop. Each carrier extends along a longitudinal axis of the assembly and is defined by a lumen that receives the corresponding shaft in sliding engagement therewith so that a proximal end of the shaft extends proximally from a proximal opening of the lumen, and so that the loop is located in proximity to a distal opening of the lumen. Each loop is collapsible from a first, maximum size thereof to a second, securing size thereof, via movement of the loop into the corresponding carrier lumen via the distal opening thereof, wherein the first size allows movement of the medical device therethrough, and the second size fits snuggly around the medical device to secure the device to the assembly.

According to aspects of this disclosure, in some examples, an assembly may include a support tube that surrounds at least a portion of first and second snares. The carriers of the first and second snares may be in sliding engagement with the support tube, such that the carriers of the first and second snares may be extended and/or retracted relative to the support tube. According to aspects of this disclosure, the support tube may provide a friction fit between the first carrier and the second carrier, which may help to hold the first and second snares in position relative to an implantable medical device unless purposefully actuated by an operator of the assembly.

According to other aspects of this disclosure, the assembly may include a pre-set offset that is established between carrier lumen distal openings. In some examples, the pre-set offset may include a spacing in a direction approximately orthogonal to the longitudinal axis of the assembly, e.g., to allow for opposing loops of first and second snares. In other examples, the pre-set offset may include a spacing in a direction approximately parallel to the longitudinal axis of the assembly, and the spacing of the pre-set offset in the direction approximately orthogonal to the longitudinal axis may be significantly smaller. In either case, the pre-set offset may allow an operator to position the first and second snare loops around the device, and, when the operator retracts the first and second snare shafts to collapse the first and second snare loops until the loops fit snuggly around the device, the pre-set offset can help to align the device with a distal-most opening of a retrieval catheter.

In one example, an assembly for retrieving an implantable medical device from an implant site includes a first snare comprising a first carrier, a first loop that is collapsible from a maximum size to a minimum size, and a first shaft, wherein the first loop is connected to a distal end of the first shaft and extends out of a distal end of the first carrier; a second snare comprising a second carrier, a second loop that is collapsible from a maximum size to a minimum size, and a second shaft, wherein the second loop is connected to a distal end of the second shaft and extends out of a distal end of the second carrier; and a support tube that surrounds at least a portion of the first carrier and the second carrier, wherein the first carrier and the second carrier are in sliding engagement with the support tube, and wherein the support tube provides a friction fit between the first carrier and the second carrier.

In another example, a method of retrieving an implantable medical device having an elongated, hermetically sealed housing includes advancing, into proximity with the implantable medical device, a retrieval assembly comprising a first snare having a first carrier, a first shaft, and a first loop that is collapsible by retracing the first shaft relative to the first carrier, a second snare having a second carrier, a second shaft, and a second loop that is collapsible by retracing the second shaft relative to the second carrier, and a support tube that surrounds at least a portion of the first carrier and the second carrier; positioning the first loop around a first portion of the implantable medical device; collapsing the first loop until the first loop fits snuggly around a first portion of the implantable medical device; positioning the second loop around a second portion of the implantable medical device, the second portion being different than the first portion; collapsing the second loop around the second portion of the implantable medical device; and retrieving the implantable medical device using the second snare

BRIEF DESCRIPTION OF THE DRAWINGS

The following drawings are illustrative of particular examples of the present invention and therefore do not limit the scope of the invention. The drawings are not to scale (unless so stated) and are intended for use in conjunction with the explanations in the following detailed description. Examples will hereinafter be described in conjunction with the appended drawings wherein like numerals denote like elements, and:

FIG. 5A is a plan view, which includes a partial cross-section, of an assembly for securing the medical device for retrieval, according to some examples;

FIG. 5B is an end view of the assembly of FIG. 5A, according to some examples;

FIG. 6A is a plan view, which includes a partial cross-section, of an assembly for securing the medical device for retrieval, according to some alternate examples;

FIG. 6B is an end view of the assembly of FIG. 6A, according to some examples;

FIGS. 10A-10D illustrate another example of an assembly for retrieving an implantable medical device from an implant site.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
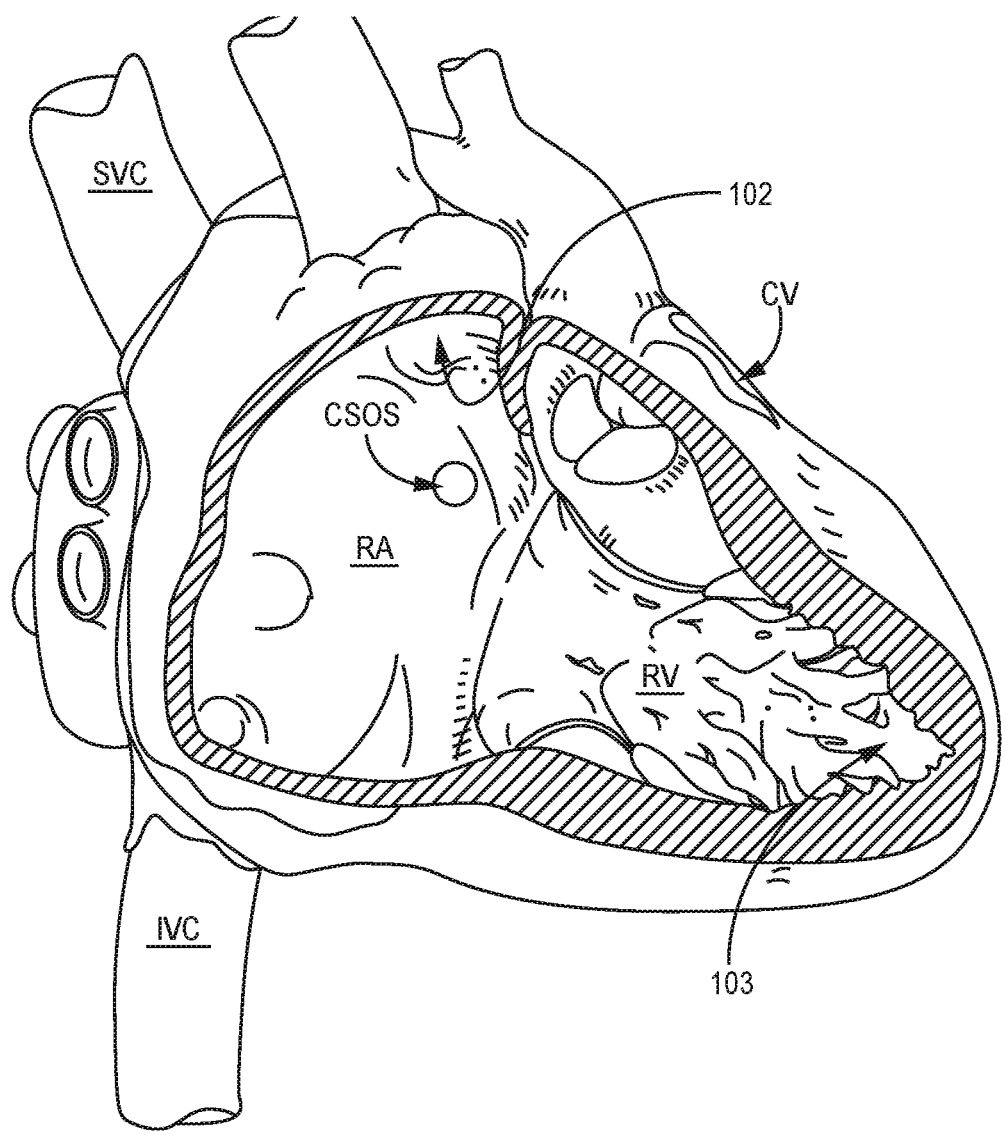
FIG. 1 is a schematic diagram showing potential implant sites for a relatively compact implantable medical device.
Figure 2:
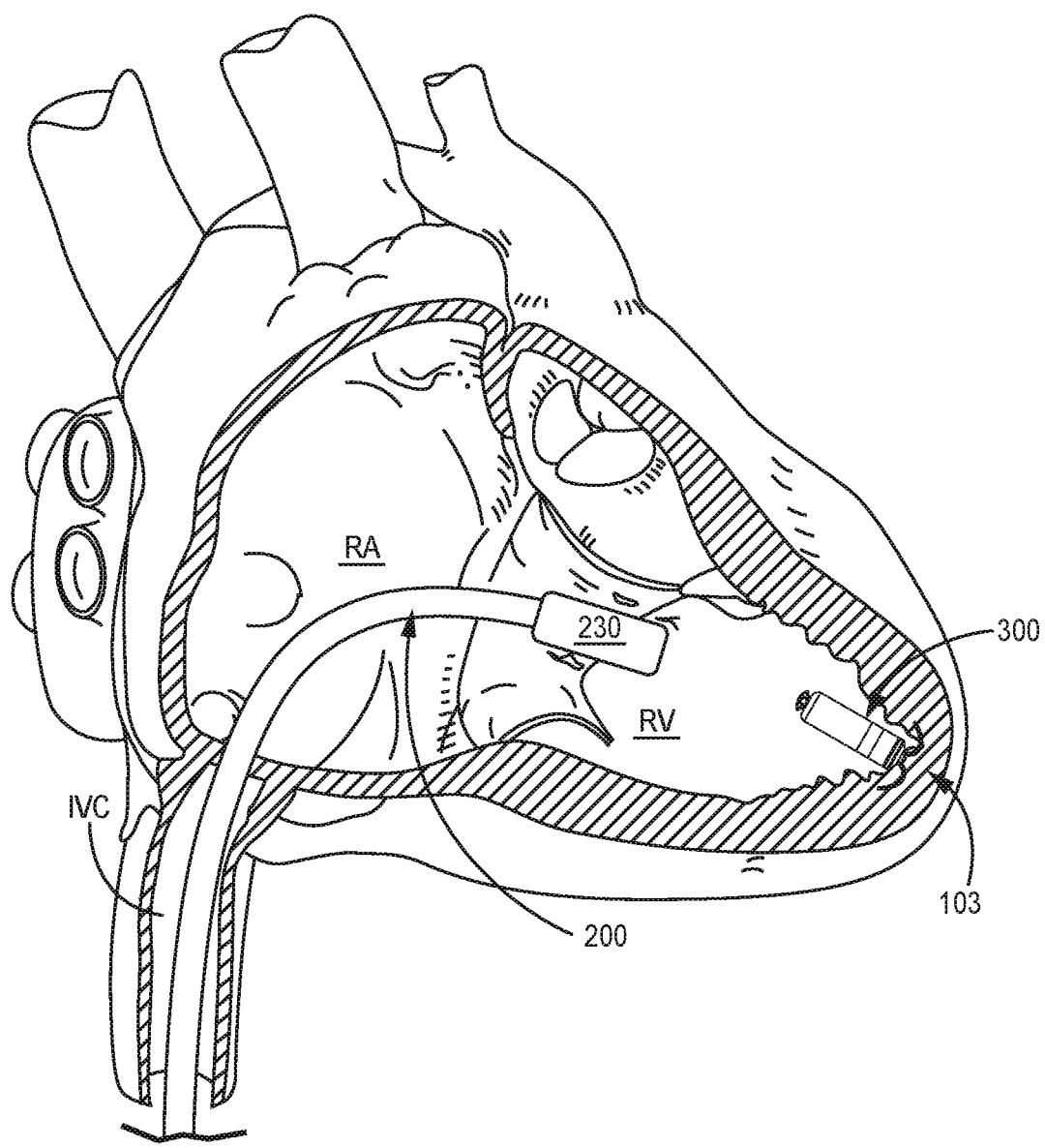
FIG. 2 is a schematic showing an exemplary relatively compact implantable medical device having been delivered from a catheter to an implant site.

FIG. 1 is a schematic diagram that shows potential cardiac implant sites for such a device, for example, within an appendage 102 of a right atrium RA, within a coronary vein CV (via a coronary sinus ostium CSOS), or in proximity to an apex 103 of a right ventricle RV, for example, as shown in FIG. 2.

FIG. 2 shows an exemplary relatively compact implantable medical device 300 having been implanted by an operator using a catheter 200, for example, like the tool described in the commonly assigned United States Patent Application Publication No. 2015/0094668, wherein the operator advanced tool 200 into the right heart through the inferior vena cava IVC, for example, from a femoral vein access site, and then deployed device 300 from a distal portion 230 of catheter 200. In some cases, when it may be necessary to retrieve the implanted device 300, the operator can employ catheter 200 to do so, but new and improved assemblies and methods may increase the ease and efficiency of retrieval.

Figure 3:
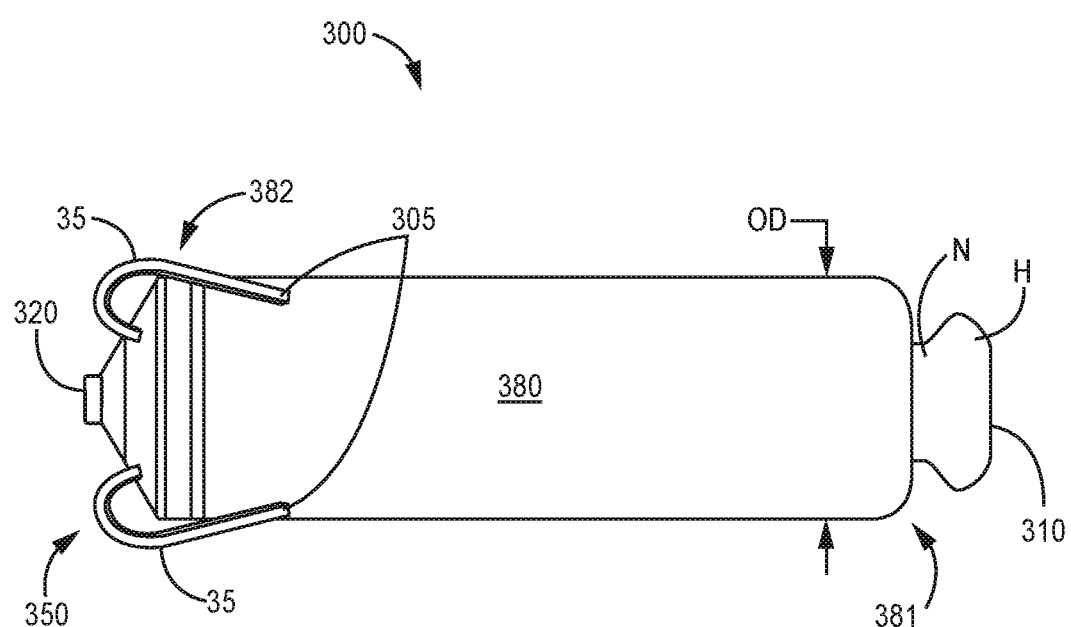
FIG. 3 is a plan view of the exemplary relatively compact implantable medical device, according to some examples.

FIG. 3 is a plan view of implantable medical device 300, according to some examples. FIG. 3 illustrates device 300 including a hermetically sealed housing 380 extending from a proximal end 381 thereof to a distal end 382 thereof, wherein a pulse generator and an associated power supply (not shown) may be contained in housing 380. Device 300 may also include an electrode 320 and a fixation member 350, both mounted in proximity to distal end 382 of housing 380, wherein electrode 320 is electrically coupled to the pulse generator via a hermetically sealed feedthrough assembly (not shown).

Housing 380, for example, formed from a biocompatible and biostable metal such as titanium, may be overlaid with an insulative layer, for example, medical grade polyurethane, parylene, or silicone, and device 300 may include another electrode (not shown), for example, formed by removing a portion of the insulative layer to expose the metallic surface of housing 380. The other electrode may function in conjunction with electrode 320 for bipolar pacing and sensing, when fixation member 350 secures electrode 320 in intimate tissue contact at a target implant site. FIG. 3 further illustrates device 300 including a snaring feature 310 joined to proximal end 381 of housing 380, wherein feature 310 includes a head H and a neck N suitably configured for engagement by a snare loop, as described below, so that device 300 can be secured for retrieval from an implant site. It should be understood that the example shown in FIG. 3 is provided for purposes of illustration only, and that an implantable medical device may have a variety of other snaring features having a variety of other properties (e.g., with neck N being replaced by wire and head H being replaced by a button, or the like).

With further reference to FIG. 3, device fixation member 350 includes a plurality of fingers 35 spaced apart from one another around a perimeter of device housing distal end 382, wherein fingers 35 are configured to fix device 300 to tissue at the implant site. Although only two fingers 35 of fixation member 350 are shown in FIG. 3, fixation member 350 may include as many as eight fingers 35. According to an exemplary example, fixation fingers 35 are integrally formed with one another, having been cut from Nitinol tubing, according to methods known in the art. After cutting the Nitinol tubing, fingers 35 may be shaped by bending and holding fingers 35 in the illustrated curvature while heat treating, according to methods known to those skilled in the art.

Fixation member 350 may be mounted to distal end 382 of device housing 380, for example, in a manner similar to that described for a fixation component 102 in commonly assigned United States Patent Application Publication No. 2012/0172690. The super-elastic nature of Nitinol allows fingers 35 to elastically deform between a relaxed condition, which is shown, and an extended condition, in which a free end 305 of each finger extends distally away from distal end 382 of device housing 380. While the illustrated example includes fixation member 350, it should be understood that other implantable medical devices may be secured to an implant site using other fixation mechanisms, such as a helical screw or the like.

Figure 4:
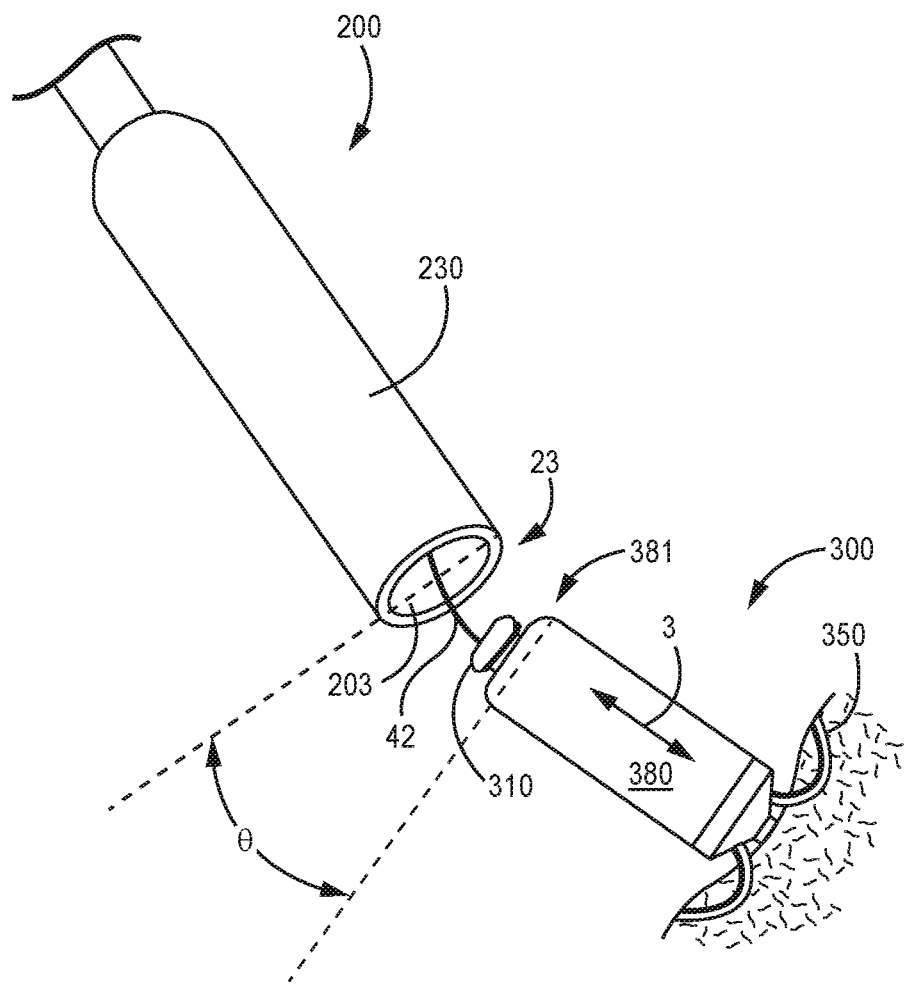
FIG. 4 is a schematic for describing a difficulty encountered in retrieving the medical device from an implant site.

FIG. 4 is a schematic that generally illustrates retrieving medical device 300 from an implant site. FIG. 4 illustrates distal portion 230 of catheter 200 located in proximity to the implant site, and a snaring assembly 42 engaging snaring feature 310 of device 300, having been passed out through a distal-most opening 203 of distal portion 230 and manipulated by an operator. Snaring assembly 42, for example, from an Amplatz Goose Neck™ snare kit (available from Medtronic), may include a collapsible loop and an elongate shaft, both being constructed from Nitinol cable to have super-elastic and shape memory properties. Once an operator has secured device 300 with snaring assembly 42, the operator may advance catheter 200 relative to snaring assembly 42 until opening 203 is brought into proximity with device housing proximal end 381, as shown.

FIG. 4 further illustrates an angle θ that corresponds to a misalignment of a plane of distal-most opening 203 of catheter distal portion 230 and a plane of proximal end 381 (approximately orthogonal to a longitudinal axis 3 of device 300). The misalignment may cause a distal-most edge 23 of distal portion 230 to catch on an edge of device proximal end 381, so that the operator may find it difficult to advance distal portion 230 over the snared device 300, or to pull the snared device 300 into distal portion 230. The angle of misalignment θ encountered in some cardiac implant sites, for example, in appendage 102 of the right atrium RA, or near apex 103 of the right ventricle RV (FIG. 1), may be greater than 45 degrees. In addition, because tissue of an implant site is often in motion (e.g., due to the beating of the heart muscle), it may be difficult for an operator to align snaring assembly 42 with snaring feature 310 of device 300.

The assemblies described herein include multiple snares that may be used, in some examples, to stabilize and/or align device 300 during retrieval. For example, according to some aspects, an assembly may include a support tube that surrounds at least a portion of first and second snares. Carriers of the first and second snares may be in sliding engagement with the support tube, such that the carriers of the first and second snares may be extended and/or retracted relative to the support tube. According to aspects of this disclosure, the support tube may provide a friction fit between the first carrier and the second carrier, which may help to hold the first and second snares in position relative to device 300 unless purposefully actuated by an operator of the assembly.

In the example above, an operator may advance a first snare over the body of device 300 and secure the first snare around the body of device 300. With device 300 stabilized by the first snare, an operator may advance a second snare over snaring feature 310 and secure the second snare around snaring feature 310. The operator may then retract device 300 into the cup of catheter 200 defined by catheter distal portion 230. In some instance, prior to retracting device 300 into the cup, the operator may release the first snare and retract the first snare such that device 300 can be retracted into the cup of catheter 200 without interference from the first snare.

According to other aspects of this disclosure, an assembly may include one or more pre-set offsets that are established between distal openings of lumens carrying the first and second snares, respectively. The pre-set offset(s) may allow an operator to position the first and second snare loops around device 300, and, when the operator retracts the first and second snare shafts to collapse the first and second snare loops until the loops fit snuggly around device 300, the pre-set offset can help to align device 300 with a distal-most opening 203, thereby reducing misalignment θ.

Figure 8A:
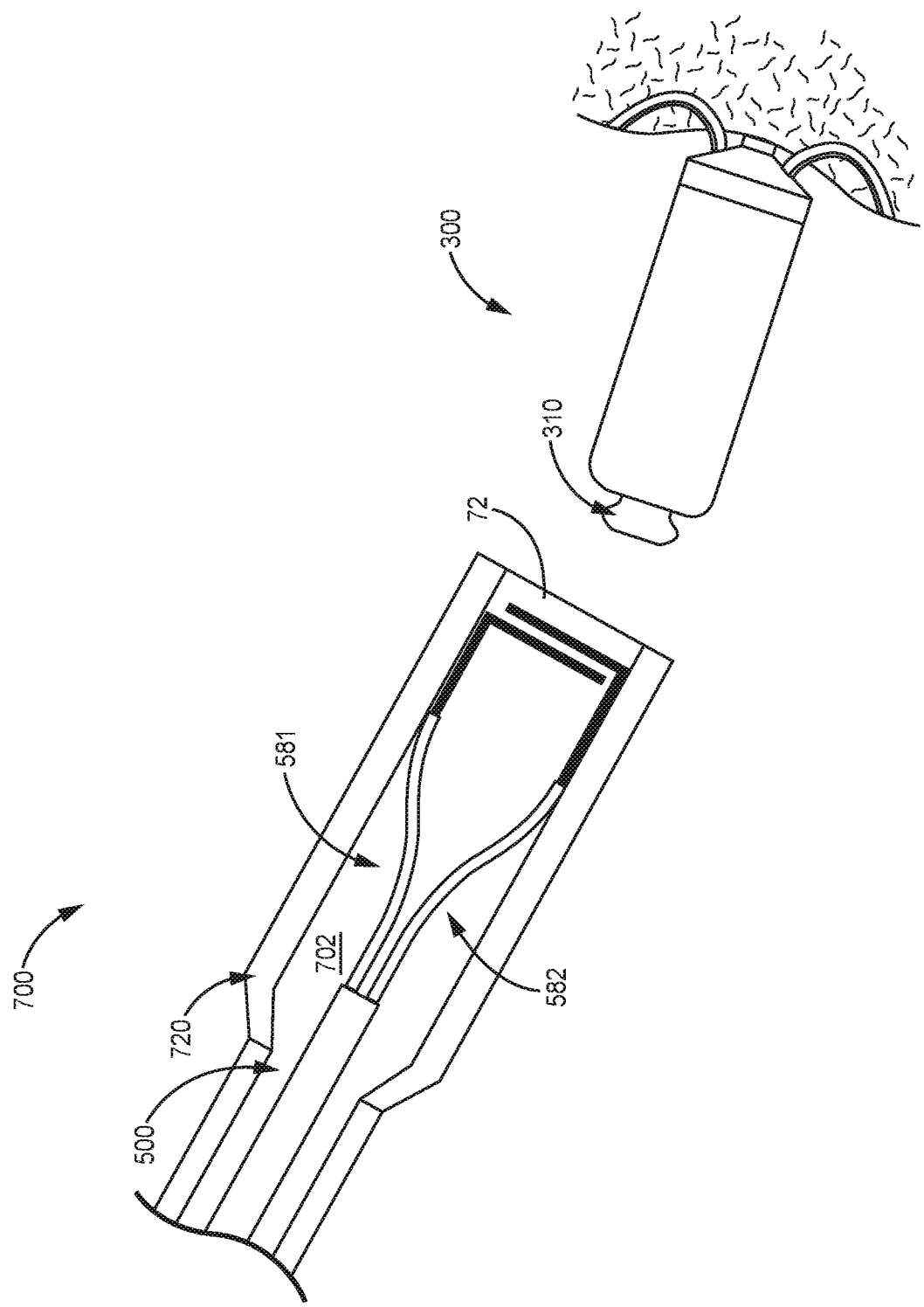
FIG. 8A is a schematic showing the assembly of FIGS. 5A-B advanced into proximity with the implanted medical device.
Figure 8B:
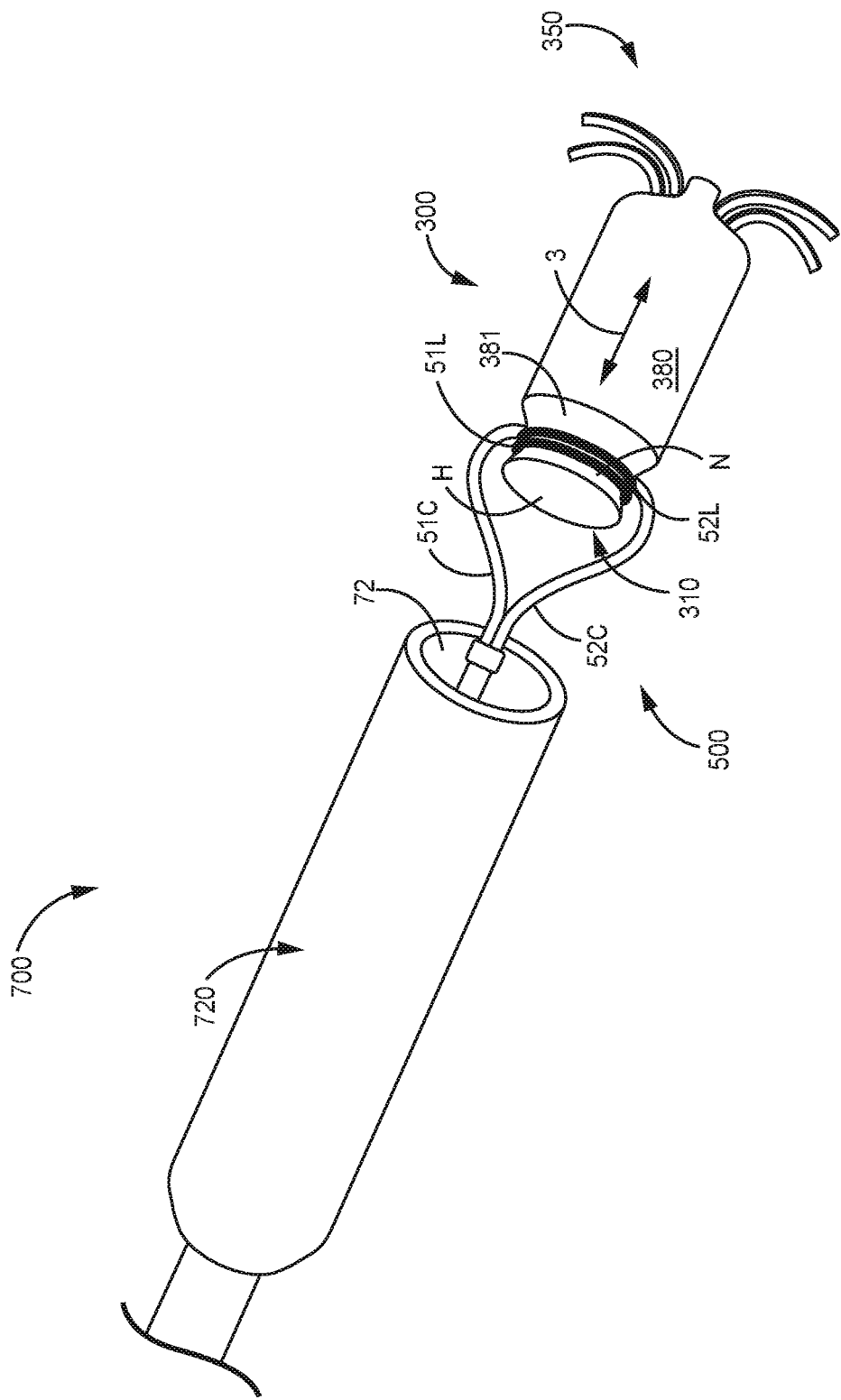
FIG. 8B is a schematic showing the assembly of FIGS. 5A-B securing the medical device for retrieval.

FIGS. 5A-B are a plan view, which includes a partial cross-section, and an end view, respectively, of an assembly 500 for securing device 300 for retrieval, according to some examples. FIG. 5A illustrates assembly 500 including a first snare 581 and a second snare 582, wherein each snare 581, 582 includes an elongate carrier 51C, 52C, a loop 51L, 52L, and an elongate shaft 51S, 52S. FIG. 5A further illustrates a distal end 512 of each shaft 51S, 52S coupled to a corresponding loop 51L, 52L, each of which extend in a plane approximately orthogonal to a longitudinal axis 5 of assembly 500 (as seen in the end view of FIG. 5B), and are collapsible from a first, maximum size to a second, securing size. The first, maximum size of loops 51L, 52L, shown in FIG. 5B, allows movement of at least a portion of medical device 300 therethrough, for example, snaring feature 310. The second, securing size fits snuggly around the portion of device 300, for example, neck N of device snaring feature 310, as shown in FIG. 8B.

According to the illustrated example, each carrier 51C, 52C extends along longitudinal axis 5 of assembly 500 and is defined by a lumen that receives a corresponding shaft 51S, 52S in sliding engagement therein. A proximal end 521 of each shaft 51S, 52S, which is shown extending proximally from a proximal opening 501 of the corresponding carrier lumen, may be engaged to retract, or move shafts 51S, 52S proximally, thereby pulling a distal end 512 of each shaft 51S, 52S and each loop 51L, 52L into the corresponding carrier lumen via a distal opening 502 thereof, which causes loops 51L, 52L to collapse from the first, maximum size.

FIGS. 5A-B illustrate each snare carrier 51C, 52C having a pre-formed curvature. The curvatures of carriers 51C, 52C establish a pre-set offset between carrier lumen distal openings 502, wherein the off-set is defined by a spacing 58 in a direction approximately orthogonal to longitudinal axis 5. With reference to FIG. 5B, the first, maximum sizes of snare loops 51L, 52L are about the same and spacing 58 of the pre-set offset is approximately equal to the first, maximum sizes.

According to one example, when head H of device snaring feature 310 has a diameter of about 0.18 inch, and an outer diameter OD of device housing 380 is about 0.263 inch (FIG. 3), spacing 58 is approximately 0.25 inch to assure that snare loops 51L, 52L can move around head H, but not around device housing 380. In FIG. 5A proximal ends 521 of snare shafts 51S, 52S are shown joined together so that an operator can move shafts 51S, 52S simultaneously; and lumen distal openings 502 of snare carriers 51C, 52C are shown approximately aligned with one another, along longitudinal axis 5, so that the simultaneous retraction, or proximal movement of shafts 51S, 52S will pull snare loops 51L, 52L almost simultaneously through respective carrier lumen distal openings 502 to collapse loops 51L, 52L.

FIGS. 5A-B further illustrate snare carriers 51C, 52C joined together, in proximity to proximal openings 501 of the lumens thereof, by an elongate tubular member 550 of assembly 500. Tubular member 550 is shown having a lumen 505 in fluid communication with the lumens of carriers 51C, 52C so that proximal ends 521 of snare shafts 51S, 52S extend therein. According to the illustrated example, assembly 500 further includes an extension 530 of shaft proximal ends 521, which extends out from a proximal opening 515 of tubular member lumen 505, to provide a means for the operator to engage and move shafts 51S, 52S as described above. Extension 530 may be formed by lengths of shaft proximal ends 521 joined together, or by another elongate shaft coupled to proximal ends 521.

FIGS. 6A-B are a plan view, which includes a partial cross-section, and an end view, respectively, of an assembly 600 for securing device 300 for retrieval, according to some examples. FIG. 6A illustrates assembly 600 including a first snare 691 and a second snare 692, wherein each snare 691, 692 includes an elongate carrier 61C, 62C, a loop 61L, 62L, and an elongate shaft 61S, 62S. FIG. 6A further illustrates a distal end 612 of each shaft 61S, 62S coupled to a corresponding loop 61L, 62L, each of which extends in a plane that is approximately orthogonal to a longitudinal axis 6 of assembly 600 (as shown in the end view of FIG. 6B), and are collapsible from a first, maximum size to a second, securing size.

The first, maximum sizes of first and second snare loops 61L, 62L, shown in FIG. 6B, allow movement of at least a portion of device 300 therethrough. The second, securing size of each, which can be seen in FIG. 9B, fits snuggly around a corresponding portion of device 300. With reference to FIG. 6B, the first, maximum size of first snare loop 61L is smaller than that of second snare loop 62L, according to some examples, and first snare loop 61L allows movement of device snaring feature 310 therethrough while second snare loop 62L allows movement of both snaring feature 310 and housing 380 of device 300 therethrough.

According to the illustrated example, each carrier 61C, 62C extends along a longitudinal axis 6 of assembly 600 and is defined by a lumen that receives a corresponding shaft 61S, 62S in sliding engagement therein. A proximal end 621 of each shaft 61S, 62S, which is shown extending proximally from a proximal opening 601 of the corresponding carrier lumen, may be engaged to retract, or move shafts 61S, 62S proximally, thereby pulling a distal end 612 of each shaft 61S, 62S and each loop 61L, 62L into the corresponding carrier lumen via a distal opening 602 thereof, which causes loops 61L, 62L to collapse from the first, maximum size.

In FIG. 6A, proximal ends 621 of shafts 61S, 62S are shown un-joined for independent movement of first and second snare shafts 61S, 62S; but, according to some alternate examples, proximal ends 621 may be joined together (as indicated with a dashed line) to facilitate simultaneous movement of first and second snare shafts 61S, 62S. FIG. 6A further illustrates first and second snare carriers 61C, 62C joined together along an entire length of first snare carrier 61C to establish a pre-set offset between distal openings 602 of first and second snare carriers 61C, 62C.

Figure 9A:
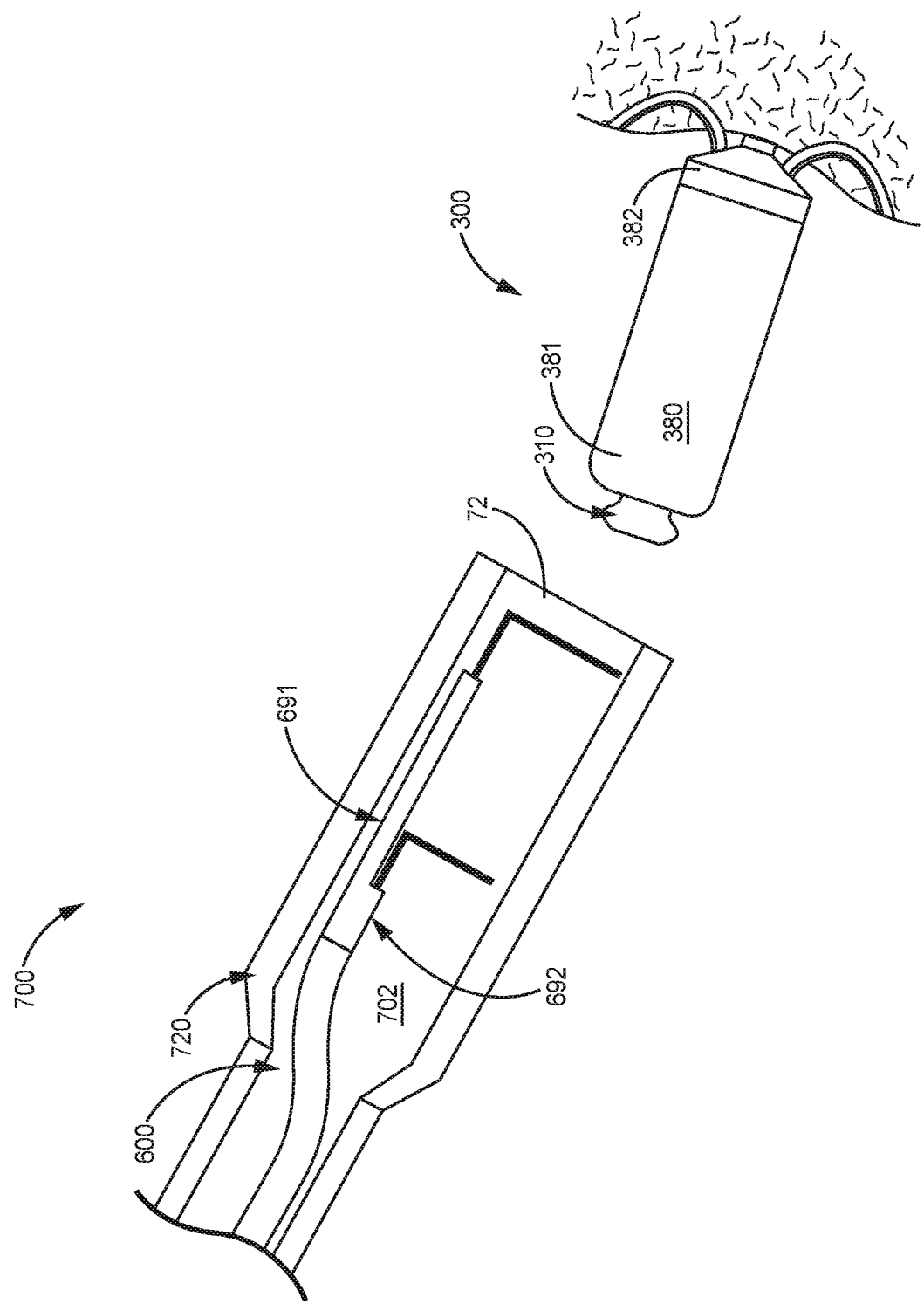
FIG. 9A is a schematic showing the assembly of FIGS. 6A-B advanced into proximity with the implanted medical device.
Figure 9B:
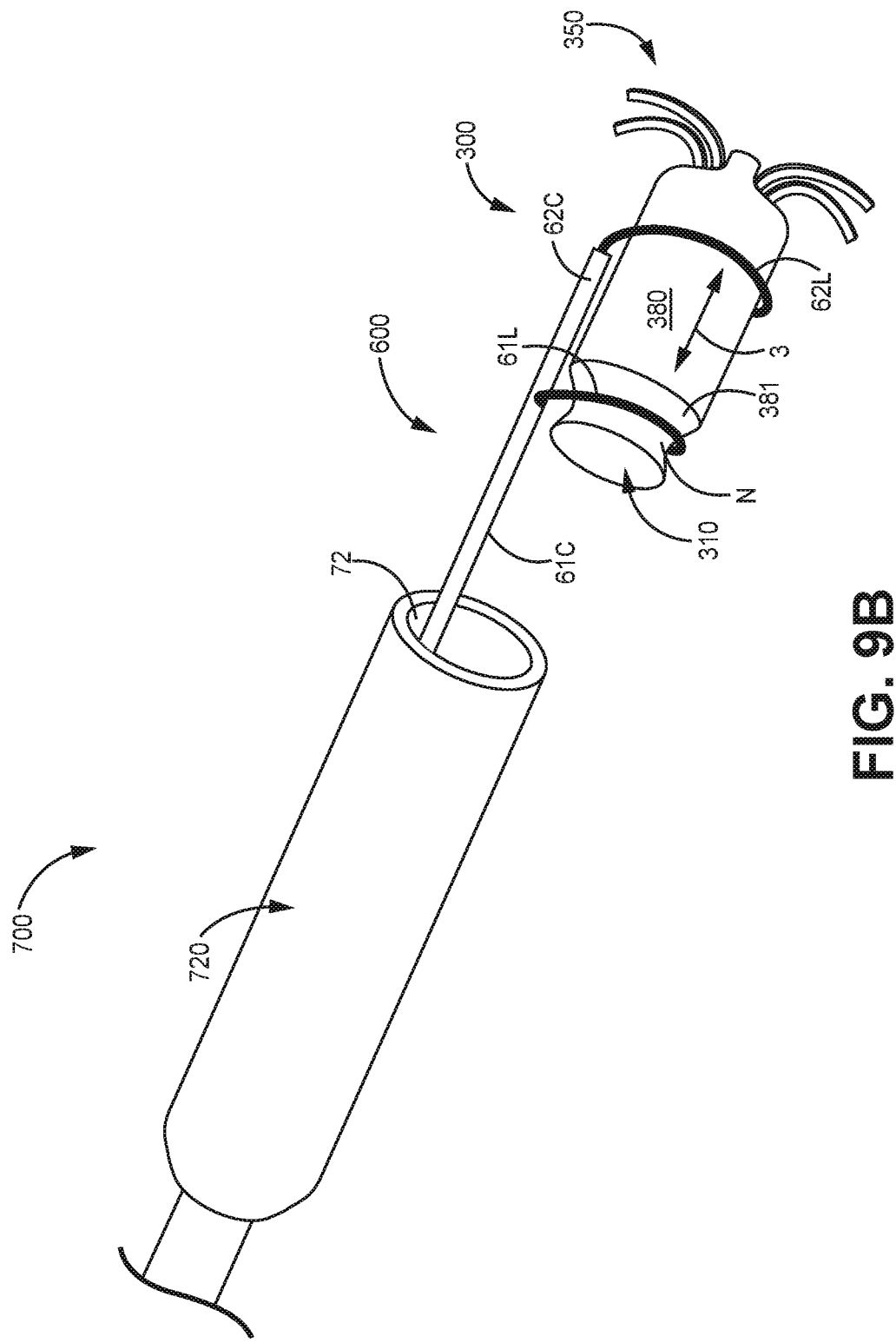
FIG. 9B is a schematic showing the assembly of FIGS. 6A-B securing the medical device for retrieval.

According to the illustrated example, the pre-set offset is defined by a first spacing 69-1 in a direction approximately orthogonal to longitudinal axis 6, and by a second spacing 69-2 in a direction approximately parallel to longitudinal axis 6. Spacings 69-1, 69-2 correspond to dimensions of device 300 to assure that when the operator positions second snare loop 62L around device housing 380, for example, approximately midway between proximal end 381 and distal end 382, the operator will have the freedom to position first snare loop 61L around neck N of device snaring feature 310, as shown in FIG. 9B. In some examples, first spacing 69-1 is approximately 0.04 inch, and second spacing 69-2 is approximately 0.45 inch.

According to some examples of assemblies 500, 600, first and second snare shafts 51S, 52S, 61S, 62S, and first and second snare loops 51L, 52L, 61L, 62L may be formed from a medical grade Nitinol wire or cable, for example, having a diameter of between approximately 0.010 inch and approximately 0.040 inch, and constructed in a similar manner to snares from the aforementioned Amplatz Goose Neck™ snare kit. First and second snare carriers 51C, 52C, 61C, 62C may be formed from any suitable medical grade polymer, for example, a polyether block amide, such as PEBAX®, or high-density polyurethane.

In assembly 500, elongate tubular member 550 may be formed from the same material of which carriers 51C, 52C are formed. Although only first and second snares 581, 582 and 691, 692 are described for assemblies 500 and 600, respectively, it should be noted that alternate examples within the scope of the present invention may include a greater number of snares. For example, with reference to FIG. 5B, an alternate example of assembly 500 may include another pair of snares configured exactly like snares 581, 582, but oriented so that the distal openings of the carrier lumens thereof are generally located at positions indicated by arrows X. And, in another example, with reference to FIGS. 6A-B, an alternate example of assembly 600 may include another snare configured like either of snares 691, 692, but positioned so that the distal opening of the carrier lumen thereof is generally located between first and second snare carrier lumen distal openings 602, within spacings 69-1 and 69-2 as generally indicated by arrows Y.

Figure 7:
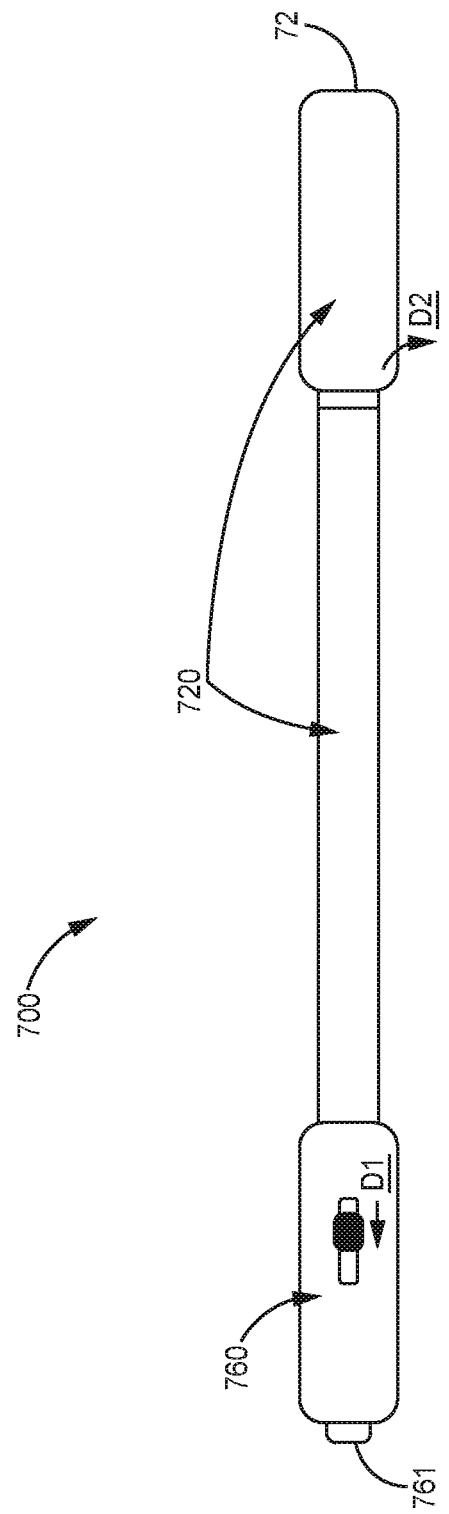
FIG. 7 is a plan view of an exemplary retrieval catheter that may be employed with any of the aforementioned assembly examples.

FIG. 7 is a plan view of an exemplary retrieval catheter 700 that may be employed with any of the above-described examples of assemblies 500, 600 or 800 (see FIGS. 10A-10C). FIG. 7 illustrates catheter 700 including an elongate tubular member 720. With reference to FIGS. 8A and 9A, tubular member 720 defines a lumen that terminates in a distal-most opening 72 and receives assemblies 500, 600 or 800 in sliding engagement therewith. FIG. 7 further illustrates a handle 760 of catheter 700 coupled to tubular member 720 and including a proximal port 761, which, according to some examples, is in fluid communication with the lumen defined by tubular member 720 to allow the extension of assemblies 500, 600, or 800 proximally therefrom so that the operator can manipulate assembly 500, 600, or 800 to secure device 300 for retrieval.

According to one example, the lumen defined by tubular member 720 has a diameter of about 0.3 inches (7.6 mm) along a limited distal length (e.g. about 31 mm) of tubular member 720, in proximity to distal-most opening 72; and, along a proximal length of tubular member 720 (e.g., about 100 cm) the lumen has a smaller diameter of about 0.154 inch (3.9 mm). The proximal length of outer tubular member 720 may be formed by a stainless steel braid-reinforced medical grade polymer, for example, one or more appropriate grades of polyether block amide, which are arranged for decreasing stiffness from handle 760 distally (e.g., PEBAX® 7233, 6333, 4033, and 3533); and the distal length of tubular member 720, which is terminated by distal-most opening 72, may be formed from a medical grade polyether block amide (e.g., PEBAX® 7233 SA-01), and includes a radiopaque marker band (not shown) integrated therein.

In some examples, catheter 700 further includes a steering assembly. With further reference to FIG. 7, the steering assembly may include a pull band mounted to tubular member 720, an actuator, which is shown mounted to handle 760, and an elongate pull wire (not shown) that extends along the proximal length of tubular member 720, wherein the pull wire has a distal end coupled to the pull band and a proximal end coupled to actuator 762, so that moving actuator 762 per arrow D1 causes the pull wire to deflect tubular member 720, in proximity to distal-most opening 72, per arrow D2. According to some methods, the steering assembly helps the operator navigate to the implant site and locate distal-most opening 72 for the retrieval of device 300, as described below.

FIG. 8A a schematic showing assembly 500 advanced into proximity with the implanted medical device 300, according to some methods in which catheter 700 is employed. FIG. 8A illustrates assembly 500 extending within lumen 702 of catheter 700, and catheter 700 having been advanced by the operator to the implant site so that catheter distal-most opening 72 is located in proximity to implanted device 300. Next, by advancing assembly 500 distally out through distal-most opening 72 of catheter, the operator may simultaneously position first and second snare loops 51L, 52L around snaring feature 310 of device 300.

This positioning may be facilitated by deflecting catheter distal-most opening 72 with the steering assembly of catheter 700, as described above.

FIG. 8B is a schematic showing assembly 500 securing device 300 for retrieval, after the operator has positioned snare loops 51L, 52L and then retracted first and second snare shafts 51S, 52S, relative to first and second snare carriers 51C, 52C. As described above, this retraction of snare shafts 51S, 52S collapses the positioned first and second snare loops 51L, 52L until they fit snuggly around neck N of device snaring feature 310. FIG. 8B further illustrates head H of device snaring feature 310 extending in between the first and second snare carriers 51C, 52C, due to the above-described pre-set offset, when snare loops 51L, 52L are positioned and collapsed, such that a plane of catheter distal-most opening 72 and a plane of device housing proximal end 381 (approximately orthogonal to device longitudinal axis 3) are approximately aligned. Thus, once the operator has secured device 300 with assembly 500, the operator can move catheter 700 distally until device 300 passes into lumen 702 through distal-most opening 72. While moving catheter 700 distally, the operator may apply a pull force through assembly 500 to disengage fixation member 350 of the secured device 300 from the implant site.

FIG. 9A is a schematic showing assembly 600 advanced into proximity with implanted medical device 300, according to some methods in which catheter 700 is employed. FIG. 9A illustrates assembly 600 extending within lumen 702 of catheter 700, and catheter 700 having been advanced by the operator to the implant site so that catheter distal-most opening 72 is located in proximity to implanted device 300. Next, by advancing assembly 600 distally out through distal-most opening 72 of catheter, the operator may position first and second snare loops 61L, 62L around device 300, so that first snare loop 61L extends around snaring feature 310 and second snare loop 62L extends around housing 380, about midway between proximal and distal ends 381, 382 thereof. This positioning may be facilitated by deflecting catheter distal-most opening 72 with the steering assembly of catheter 700, as described above.

FIG. 9B is a schematic showing assembly 600 securing medical device 300 for retrieval, after the operator has positioned snare loops 61L, 62L and then retracted first and second snare shafts 61S, 62S, relative to first and second snare carriers 61C, 62C. As described above, this retraction of snare shafts 61S, 62S, either independently or simultaneously, collapses the positioned first and second snare loops 61L, 62L until first snare loop 61L fits snuggly around neck N of device snaring feature 310 and second snare loop 62L fits snuggly around device housing 380. According to some methods, the operator retracts second snare shaft 62S to collapse second snare loop 62L around device housing 380, before retracting first snare shaft 61S to collapse first snare loop 61L around neck N of device snaring feature 310.

In either case, due to the above-described pre-set offset, second snare carrier 62C extends alongside device snaring feature 310 and device housing 380, while a length of device 300 is secured by first and second loops 61L, 62L, such that a plane of catheter distal-most opening 72 and a plane of device housing proximal end 381 (approximately orthogonal to device longitudinal axis 3) are approximately aligned. Thus, once the operator has secured device 300 with assembly 600, the operator can move catheter 700 distally until device 300 passes into lumen 702 through distal-most opening 72. While moving catheter 700 distally, the operator may apply a pull force through assembly 600 to disengage fixation member 350 of the secured device 300 from the implant site.

FIG. 10A-10D illustrate another example of an assembly 800 for retrieving an implantable medical device from an implant site. For example, FIG. 10A illustrates a plan view of assembly 800, while FIGS. 10B and 10C illustrate example end views of assembly 800. FIG. 10D illustrates assembly 800 extending from a cup of a delivery catheter, such as tubular member 720 terminating in a distal-most opening 72, as illustrated by FIGS. 8A-9B.

In the example illustrated by FIG. 10A, assembly 800 includes a first snare 802 having a first carrier 804, a first loop 806 and a first shaft 808. First loop 806 is connected to a distal end of first shaft 808 and extends out of a distal end of first carrier 804. As described above with respect to assemblies 500, 600, first snare 802 may be constructed in a similar manner to snares from the aforementioned Amplatz Goose Neck™ snare kit. For example, first carrier 804 may be formed from any suitable medical grade polymer, for example, a polyether block amide, such as PEBAX®, or high-density polyurethane. First loop 806 and first shaft 808 may be formed from a medical grade Nitinol wire or cable. The wire or cable may have a diameter of between approximately 0.010 inches and approximately 0.040 inches, but may vary based on the particular construction of the implantable medical device being retrieved (e.g., relatively larger wires or cables may be used to retrieve relatively larger implantable medical devices).

Assembly 800 also includes a second snare 810 having a second carrier 812, a second loop 814 and a second shaft 816. Second loop 814 is connected to a distal end of second shaft 816 and extends out of a distal end of second carrier 812. In some examples, second snare 810 may be configured similarly to first snare 802, e.g., being composed of the same or similar materials.

First loop 806 and second loop 814 may each be collapsible from a maximum size to a minimum size. In some examples, a maximum size of first loop 806 may be greater than a maximum size of second loop 814. For example, second snare 810 may be configured to grasp a relatively smaller feature, e.g., such as snaring feature 310 of device 300, than first snare 802. Hence, in some instances, second snare 810 may have a relatively smaller loop and/or a smaller carrier than first snare 802. In one example, first loop 806 is approximately 16 mm in diameter (e.g., plus or minus 4 mm) and second loop is approximately 7 mm in diameter (e.g., plus or minus 2 mm), while first carrier 804 is approximately 6.0 French catheter size and the second carrier is approximately 2.3-3.0 French catheter size.

Assembly 800 also includes a support tube 820 that surrounds at least a portion of first carrier 804 and second carrier 812. In the illustrated example, support tube 820 surrounds the majority of the length of first carrier 804 and second carrier 812. In other examples, support tube 820 may surround a relatively shorter portion of first carrier 804 and second carrier 812. Support tube 820 may be composed of any suitable medical grade polymer, for example, a polyether block amide, such as PEBAX®, or high-density polyurethane. In some examples, as shown in the example of FIG. 10B, support tube 820 may be composed of a relatively flexible material that deforms around first carrier 804 and second carrier 812, thereby producing an oblong shape. In other examples, support tube 820 may be relatively rigid and/or have a generally circular shape.

According to aspects of this disclosure, support tube 820 is sized such that at least one of first carrier 804 and second carrier 812 are in sliding engagement with support tube 820. Support tube 820 is also sized to provide a friction fit between first carrier 804 and second carrier 812. That is, first carrier 804 and/or second carrier 812 may be moveable relative to support tube 820, but support tube 820 may compress first carrier 804 and/or second carrier 812 such that support tube 820, first carrier 804 and second carrier 812 move as a single unit unless an operator initiates independent movement of first carrier 804 and second carrier 812.

In some instances, only one of first carrier 804 or second carrier 812 may be moveable with respect to support tube 820. For example, one of first carrier 804 or second carrier 812 may be coupled to or integrated with support tube 820. In this example, the other of first carrier 804 or second carrier 812 may remain in sliding engagement. In other instances, both first carrier 804 and second carrier 812 are moveable with respect to support tube 820.

As shown in FIG. 10B, in some examples, support tube 820 includes a septum 822 that separates first carrier 804 and second carrier 812. That is, septum 822 defines a first lumen through which first carrier 804 passes and a second lumen through which second carrier 812 passes. In other examples, support tube 820 may not include septum 822 such that support tube 820 defines a single lumen through which both first carrier 804 and second carrier 812 pass.

According to aspects of this disclosure, assembly 800 may include an alignment feature that aligns the first loop and the second loop such that the first loop and the second loop are concentric. In some examples, extrusions or other features may be incorporated in first carrier 804 and second carrier 812 to maintain alignment.

FIG. 10C illustrates one example of an alignment feature that includes a first profile extrusion 830 of first carrier 804 and a corresponding first keyed extrusion 832 on first shaft 808. According to aspects of this disclosure, first keyed extrusion 832 is in sliding engagement with first profile extrusion 830, such that first shaft 808 is moveable within first carrier 804 but cannot significantly rotate within first carrier 804. In addition, the illustrated example of the alignment feature includes a second profile extrusion 834 of second carrier 812 and a corresponding second keyed extrusion 836 on second shaft 816. Second keyed extrusion 836 is in sliding engagement with second profile extrusion 834, such that second shaft 816 is moveable within second carrier 812 but cannot significantly rotate within second carrier 812. Because the first and second extrusion/keys for the first and second snares 802, 810 are in alignment, first loop 806 maintains alignment with second loop 814.

Hence, the illustrated example includes an alignment feature having a profile extrusion 830 and corresponding keyed extrusion 832 on first carrier 804 and first shaft 808, respectively, that is aligned with a profile extrusion 834 and corresponding keyed extrusion 836 on second carrier 812 and second shaft 816, respectively. In some examples, the alignment feature may run the entire length of first carrier 804/second carrier 812. In other examples, the alignment feature may be significantly shorter, but may include a stop the prevents the keyed portion from being removed from the extrusion.

It should be understood that the illustrated example is just one example of potential alignment features, and that other examples are possible. For instance, while the illustrated example includes keyed extrusions having two splines, any number of splines may be included to maintain alignment. A variety of other extrusions that may be used as an alignment feature are explained, for example, in commonly assigned U.S. Pat. No. 7,130,700.

In some examples, assembly 800 may include an offset feature that establishes a minimum pre-set offset between a distal end of the first shaft and the distal end of the second shaft. For example, in the example illustrated by FIG. 10A, the distal end of first carrier 804 (nearest loop 806) extends relatively further than the distal end of second carrier 812, as illustrated by arrow 822. In some examples, the offset feature may include a stop (e.g. a projection that prevents first carrier 804 from moving relative to second carrier 812 beyond a predetermined amount) at the proximal or distal ends of first carrier 804 or second carrier 812. In some instances, assembly 800 may also include a stop that prevents first carrier 804 and second carrier 812 from being fully withdrawn from support tube 820.

Proximal ends of first shaft 808 and second shaft 816 are shown un-joined for independent movement of first shaft 808 and second shaft 816. However, in other examples, the proximal ends may be joined together (as indicated with a dashed line) to facilitate simultaneous movement of first shaft 808 and second shaft 816.

Figure 11:
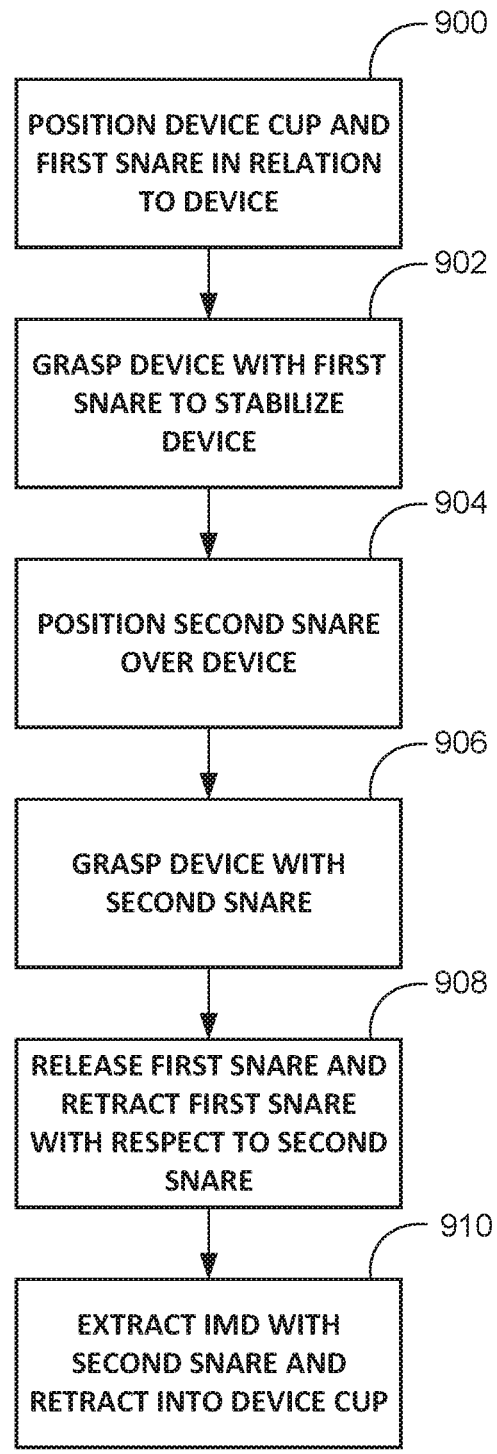
FIG. 11 is a flow chart that illustrates a process for retrieving an implantable medical device.

FIG. 11 is a flow chart that illustrates a process for retrieving an implantable medical device, such as device 300. While described with respect to assembly 800, it should be understood that the process described with respect to the example of FIG. 11 may be carried out using a variety of other assemblies, e.g., assembly 500 or assembly 600.

An operator advances assembly 800 into proximity with an implantable medical device (e.g., such as device 300), thereby positioning a device cup (e.g., such as tubular member 720) and first snare 802 in relation to device 300 (900). The operator positions first loop 806 around a first portion of device 300, such as a body of device 300 (902). The operator collapses first loop 806 until first loop 806 fits snuggly around the first portion of device 300 (904). For example, collapsing first loop 806 may be achieved by advancing first carrier 804 with respect to second carrier 812 and support tube 820 until first carrier 804 extends over at least a portion of first loop 806.

After securing first loop 806 around device 300, the operator may position second loop 814 around a second portion of device 300, e.g., around snaring feature 310 (904). In some instances, first loop 806 may stabilize device 300 such that second loop 814 may be appropriately positioned. The operator collapses second loop 814 until second loop 814 fits snuggly around the second portion of device 300 (906). For example, collapsing second loop 814 may be achieved by advancing second carrier 812 with respect to first carrier 804 and support tube 820 until second carrier 812 extends over at least a portion of second loop 814.

In some examples, according to aspects of this disclosure, the operator may then release first loop 806 from engagement with device 300 and retract first loop 806 with respect to second loop 814 (908). For example, with second loop 814 secure around device 300, the operator may move first loop 806 out of the way such that device 300 can be retracted into tubular member 720 without interference between first loop 814 and tubular member 720.

The operator may then retrieve device 300 using the second snare 810. For example, operator may apply a pulling force at the proximal end of second shaft 816 that pulls device 300 toward and into tubular member 720.

In the foregoing detailed description, the invention has been described with reference to specific examples. However, it may be appreciated that various modifications and changes can be made without departing from the scope of the invention as set forth in the appended claims.

What is claimed is:

1. An assembly for retrieving an implantable medical device from an implant site, the assembly defining a longitudinal axis, and the assembly comprising:
   a first snare comprising a first carrier, a first loop that is collapsible from a first maximum size to a first minimum size, and a first shaft, wherein the first loop is connected to a distal end of the first shaft and extends out of a distal end of the first carrier, and wherein a perimeter of the distal end of the first carrier defines a first displacement orthogonal to the longitudinal axis;
   a second snare comprising a second carrier, a second loop that is collapsible from a second maximum size to a second minimum size, and a second shaft, wherein the second loop is connected to a distal end of the second shaft and extends out of a distal end of the second carrier,
   wherein a perimeter of the distal end of the second carrier defines a second displacement orthogonal to the longitudinal axis,
   wherein the first carrier and the second carrier extend along the longitudinal axis,
   wherein the first loop is configured to extend from the distal end of the first shaft in a first plane approximately orthogonal to the longitudinal axis when the distal end of the first shaft extends out of the distal end of the first carrier, wherein the first loop defines a displacement in the first plane greater than the first displacement added to the second displacement when the first loop extends in the first plane,
   wherein the second loop is configured to extend from the distal end of the second shaft in a second plane approximately orthogonal to the longitudinal axis when the distal end of the second shaft extends out of the distal end of the second carrier,
   wherein the assembly defines a pre-set offset between the distal end of the first carrier and the distal end of the second carrier, and
   wherein the pre-set offset defines a spacing in a direction approximately parallel to the longitudinal axis; and
   a delivery catheter defining a lumen and a distal most opening to the lumen, wherein the delivery catheter is configured to position the assembly within the lumen when the first loop extends in the first plane and the second loop extends in the second plane.

2. The assembly of claim 1, further comprising a support tube, wherein the support tube comprises a single lumen that surrounds the first carrier and the second carrier.

3. The assembly of claim 1, further comprising a support tube, wherein the support tube comprises a lumen surrounding at least a portion of the first carrier and at least a portion of the second carrier.

4. The assembly of claim 1, wherein the first maximum size of the first loop is greater than the second maximum size of the second loop.

5. The assembly of claim 1, wherein the first loop is approximately 20 mm in diameter and the second loop is approximately 7 mm in diameter.

6. The assembly of claim 1, wherein the first carrier is approximately 6.0 French and the second carrier is approximately 2.3-3.0 French.

7. The assembly of claim 1, further comprising an alignment feature that aligns the first loop and the second loop such that the first loop and the second loop are concentric.

8. The assembly of claim 7, wherein the alignment feature comprises a profile extrusion and corresponding keyed extrusion on the first carrier and the first shaft, respectively, that is aligned with a profile extrusion and corresponding keyed extrusion on the second carrier and the second shaft, respectively.

9. The assembly of claim 1, further comprising a support tube, wherein the support tube surrounds the first carrier and the second carrier along the length of the first carrier and the second carrier.

10. The assembly of claim 1, further comprising a support tube, wherein the support tube comprises a stop that prevents the first carrier and the second carrier from being fully withdrawn from the support tube.

11. The assembly of claim 1, wherein the assembly defines a second pre-set offset between the distal end of the first carrier and the distal end of the second carrier, wherein the second pre-set offset defines a spacing in a direction approximately orthogonal to the longitudinal axis.

12. The assembly of claim 1, wherein the pre-set offset defined by the assembly is configured to align a proximal end of the implantable medical device with a distal-most opening to a lumen defined by a catheter when:
   the assembly extends through the distal-most opening of the catheter,
   the first loop is positioned around the implantable medical device, and
   the second loop is positioned around a housing of the implantable medical device distal to the first loop, wherein the housing is between the proximal end of the implantable medical device and a distal end of the implantable medical device,
   wherein the assembly is configured to position the implantable medical device within the lumen when the first loop is positioned around the implantable medical device and the second loop is positioned around the housing of the implantable medical device and the catheter translates to position the assembly in the lumen.

13. The assembly of claim 1, wherein the second loop defines a displacement in the second plane greater than the first displacement added to the second displacement when the second loop extends in the second plane.

14. A method of retrieving an implantable medical device having an elongated, hermetically sealed housing, the method comprising:
   advancing, into proximity with the implantable medical device, a retrieval assembly defining a longitudinal axis by retracting a first shaft relative to the first carrier and retracting a second shaft relative to a second carrier, the retrieval assembly comprising:
   a first snare having the first carrier, the first shaft, and a first loop that is collapsible from a first maximum size to a first minimum size by retracting the first shaft relative to the first carrier, wherein the first loop is connected to a distal end of the first shaft and extends out of a distal end of the first carrier, wherein a perimeter of the distal end of the first carrier defines a first displacement orthogonal to the longitudinal axis, and
   a second snare having the second carrier, the second shaft, and a second loop that is collapsible from a second maximum size to a second minimum size by retracting the second shaft relative to the second carrier, wherein the second loop is connected to a distal end of the second shaft and extends out of a distal end of the second carrier, wherein a perimeter of the distal end of the second carrier defines a second displacement orthogonal to the longitudinal axis, wherein the first carrier and the second carrier extend along the longitudinal axis, wherein the first loop extends from the distal end of the first shaft in a first plane approximately orthogonal to the longitudinal axis when the distal end of the first shaft extends out of the distal end of the first carrier, wherein the first loop defines a displacement in the first plane greater than the first displacement added to the second displacement when the first loop extends in the first plane, wherein the second loop is configured to extend from the distal end of the second shaft in a second plane approximately orthogonal to the longitudinal axis when the distal end of the second shaft extends out of the distal end of the second carrier, wherein the assembly defines a pre-set offset between the distal end of the first carrier and the distal end of the second carrier, and wherein the pre-set offset defines a spacing in a direction approximately parallel to the longitudinal axis;

positioning the first loop around a first portion of the implantable medical device;

collapsing the first loop until the first loop fits snuggly around a first portion of the implantable medical device;

positioning the second loop around a second portion of the implantable medical device, the second portion being different than the first portion;

collapsing the second loop around the second portion of the implantable medical device;

aligning a proximal end of the implantable medical device with a distal-most opening of a catheter when the first loop positions around the first portion and the second loop positions around the second portion, wherein the retrieval assembly extends from the distal-most opening of the catheter, wherein the distal-most opening opens to a lumen defined by the catheter, and wherein the catheter is configured to position the assembly within the lumen when the first loop extends in the first plane and the second loop extends in the second plane; and retrieving the implantable medical device using the second snare.

15. The method of claim 14, further comprising, prior to retrieving the implantable medical device using the second snare, releasing the first snare and retracting the first snare such that the first snare is positioned further toward the assembly than the second snare.

16. The method of claim 14, wherein retrieving the implantable medical device using the second snare comprises applying a pulling force to the second shaft sufficient to move the implantable medical device into a device cup of a catheter carrying the assembly.

17. The method of claim 14, wherein positioning the first loop around the first portion of the implantable medical device comprises advancing the first shaft with respect to the first carrier.

18. The method of claim 14, wherein positioning the second loop around the second portion of the implantable medical device comprises advancing the second shaft with respect to the second carrier.

19. The method of claim 14, wherein collapsing the first loop comprises advancing the first carrier with respect to the second carrier until the first carrier extends over at least a portion of the first loop.

20. The method of claim 14, wherein collapsing the second loop comprises advancing the second carrier with respect to the first carrier until the second carrier extends over at least a portion of the second loop.

* * * * *